United States Patent [19]
Urban et al.

[11] Patent Number: 5,860,996
[45] Date of Patent: *Jan. 19, 1999

[54] OPTICAL TROCAR

[75] Inventors: Carl T. Urban, Lake Oswego, Oreg.;
Marc J. Theroux, Bethel, Conn.;
Maria E. Lopez-Isa, Shelton, Conn.;
Jo Ann Bryan, Norwalk, Conn.

[73] Assignee: United States Surgical Corporation, Norwalk, Conn.

[ * ] Notice: This patent issued on a continued prosecution application filed under 37 CFR 1.53(d), and is subject to the twenty year patent term provisions of 35 U.S.C. 154(a)(2).

[21] Appl. No.: 841,023

[22] Filed: Apr. 29, 1997

Related U.S. Application Data

[63] Continuation of Ser. No. 249,707, May 26, 1994, abandoned.

[51] Int. Cl.⁶ .............................. A61B 17/34; A61M 5/00
[52] U.S. Cl. ............................................. 606/185; 604/261
[58] Field of Search ...................................... 604/164, 264; 606/167, 170, 174, 184, 185; 600/101

[56] References Cited

U.S. PATENT DOCUMENTS

| | | |
|---|---|---|
| 1,380,447 | 6/1921 | Wescott . |
| 1,727,495 | 9/1929 | Wappler . |
| 2,699,770 | 1/1955 | Fourestier et al. . |
| 2,764,148 | 9/1956 | Sheldon . |
| 2,764,149 | 9/1956 | Sheldon . |
| 2,877,368 | 3/1959 | Sheldon . |
| 3,021,834 | 2/1962 | Sheldon . |
| 3,417,745 | 12/1968 | Sheldon . |
| 3,437,747 | 4/1969 | Sheldon . |
| 3,499,107 | 3/1970 | Sheldon . |
| 3,538,916 | 11/1970 | Wiles . |
| 3,556,085 | 1/1971 | Takahashi . |
| 3,762,416 | 10/1973 | Moss et al. . |
| 3,809,095 | 5/1974 | Cimber . |
| 3,915,169 | 10/1975 | McGuire . |
| 3,961,621 | 6/1976 | Northeved . |
| 4,210,146 | 7/1980 | Banko . |
| 4,220,155 | 9/1980 | Kimberling et al. . |

(List continued on next page.)

FOREIGN PATENT DOCUMENTS

| | | |
|---|---|---|
| 0135364 | 3/1985 | European Pat. Off. . |
| 0433581 | 6/1991 | European Pat. Off. . |
| 0484725 | 5/1992 | European Pat. Off. . |
| 0604197 | 6/1994 | European Pat. Off. . |
| 0642764 | 3/1995 | European Pat. Off. . |
| 2697150 | 4/1994 | France . |
| 1616107 | 4/1971 | Germany . |
| 2922239 | 3/1982 | Germany . |
| 9112976 | 12/1991 | Germany . |
| 4133073 | 4/1992 | Germany . |
| 4035146 | 5/1992 | Germany . |
| 537677 | 12/1976 | Russian Federation . |
| 942730 | 7/1982 | Russian Federation . |
| 719538 | 12/1954 | United Kingdom . |
| 1215383 | 12/1970 | United Kingdom . |
| 2048686 | 12/1980 | United Kingdom . |
| 9214514 | 9/1992 | WIPO . |

OTHER PUBLICATIONS

Copy of European Search Report dated Nov. 8, 1995.

*Primary Examiner*—Glenn K. Dawson

[57] ABSTRACT

A blade actuating assembly is provided which permits selective reciprocal movement of a tissue cutting blade positioned at a distal end of an optical trocar assembly from a non-deployed position to a deployed position and back to a non-deployed position. The trocar assembly has an optical obturator which includes a sleeve having a longitudinal bore between a proximal end and a distal end. The longitudinal bore of the sleeve is configured to receive at least a portion of an endoscope or like image transferring system. An objective optical member, such as an optical window is positioned at the distal end of the sleeve and is provided to permit optical images to pass into the longitudinal bore of the sleeve and to permit illumination light to pass to the surgical site.

23 Claims, 6 Drawing Sheets

U.S. PATENT DOCUMENTS

| | | |
|---|---|---|
| 4,254,762 | 3/1981 | Yoon . |
| 4,256,119 | 3/1981 | Gauthier . |
| 4,269,192 | 5/1981 | Matsuo . |
| 4,345,589 | 8/1982 | Hiltebrandt . |
| 4,411,653 | 10/1983 | Razi . |
| 4,790,312 | 12/1988 | Capuano, Sr. et al. . |
| 4,865,029 | 9/1989 | Pankratov et al. . |
| 4,904,246 | 2/1990 | Atkinson . |
| 4,957,112 | 9/1990 | Yokoi et al. ............................... 128/4 |
| 4,961,414 | 10/1990 | Cho et al. . |
| 4,962,770 | 10/1990 | Agee et al. . |
| 4,976,269 | 12/1990 | Mehl . |
| 4,991,600 | 2/1991 | Taylor . |
| 5,066,288 | 11/1991 | Deniega et al. . |
| 5,089,000 | 2/1992 | Agee et al. . |
| 5,092,872 | 3/1992 | Segalowitz . |
| 5,104,382 | 4/1992 | Brinkerhoff et al. . |
| 5,116,353 | 5/1992 | Green . |
| 5,275,583 | 1/1994 | Crainich ................................. 606/167 |
| 5,334,150 | 8/1994 | Kaali ..................................... 606/185 |
| 5,354,302 | 10/1994 | Ko . |
| 5,372,588 | 12/1994 | Farley et al. ............................ 606/167 |
| 5,376,076 | 12/1994 | Kaali ..................................... 606/185 |
| 5,380,291 | 1/1995 | Kaali ..................................... 606/185 |
| 5,385,572 | 1/1995 | Nobles et al. . |
| 5,441,041 | 8/1995 | Sauer et al. . |
| 5,445,142 | 8/1995 | Hassler, Jr. . |
| 5,467,762 | 11/1995 | Sauer et al. ............................. 604/164 |

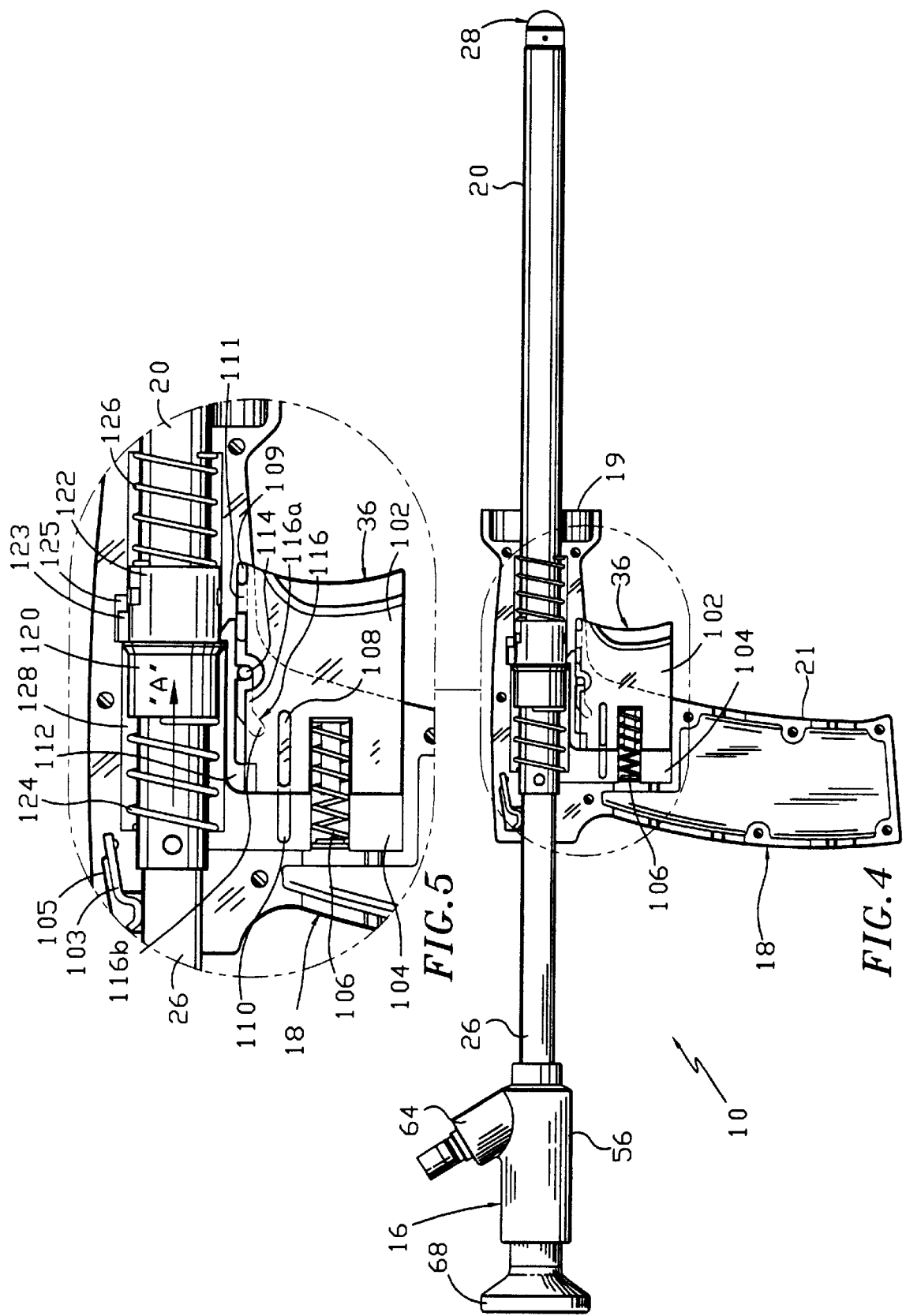

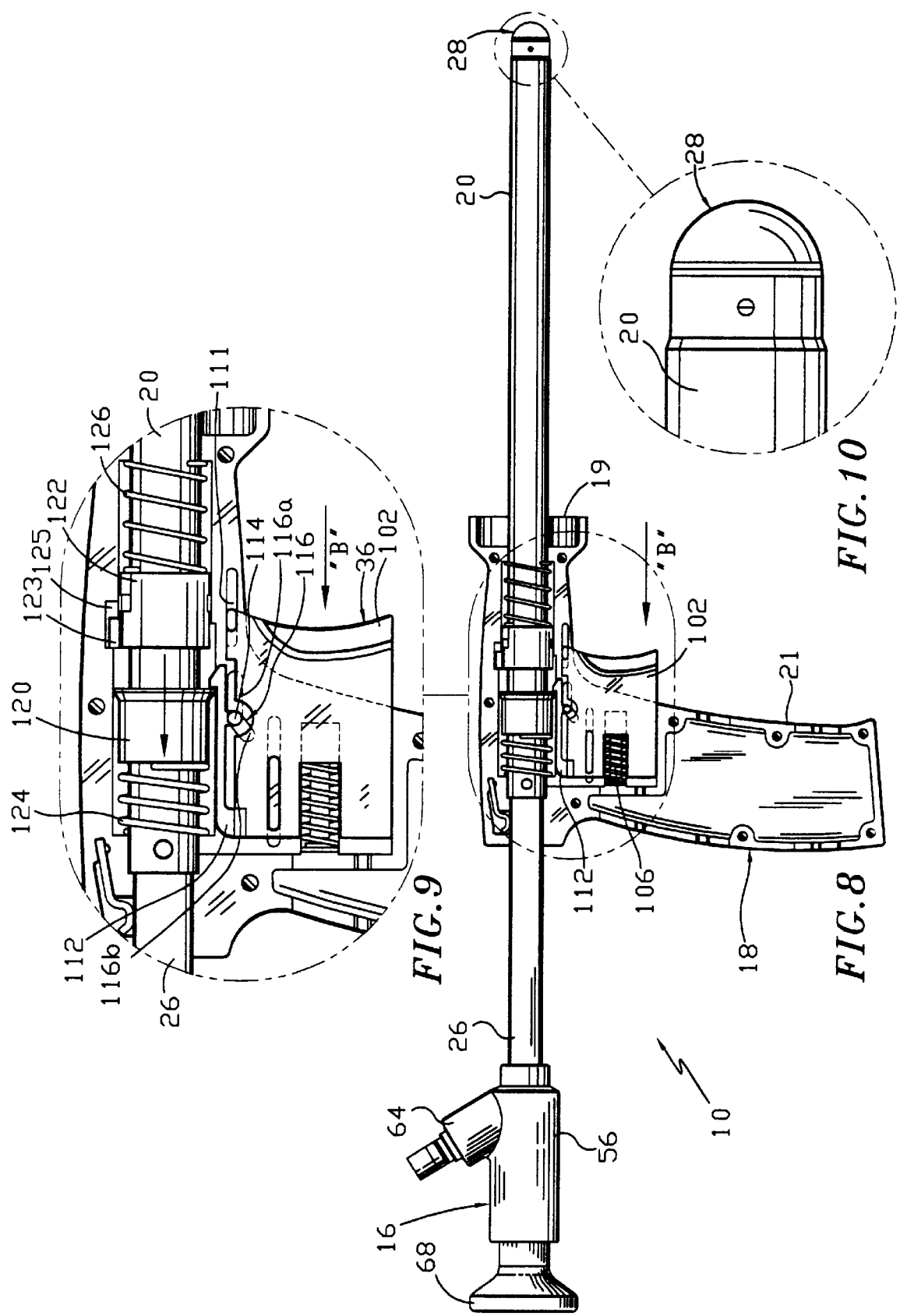

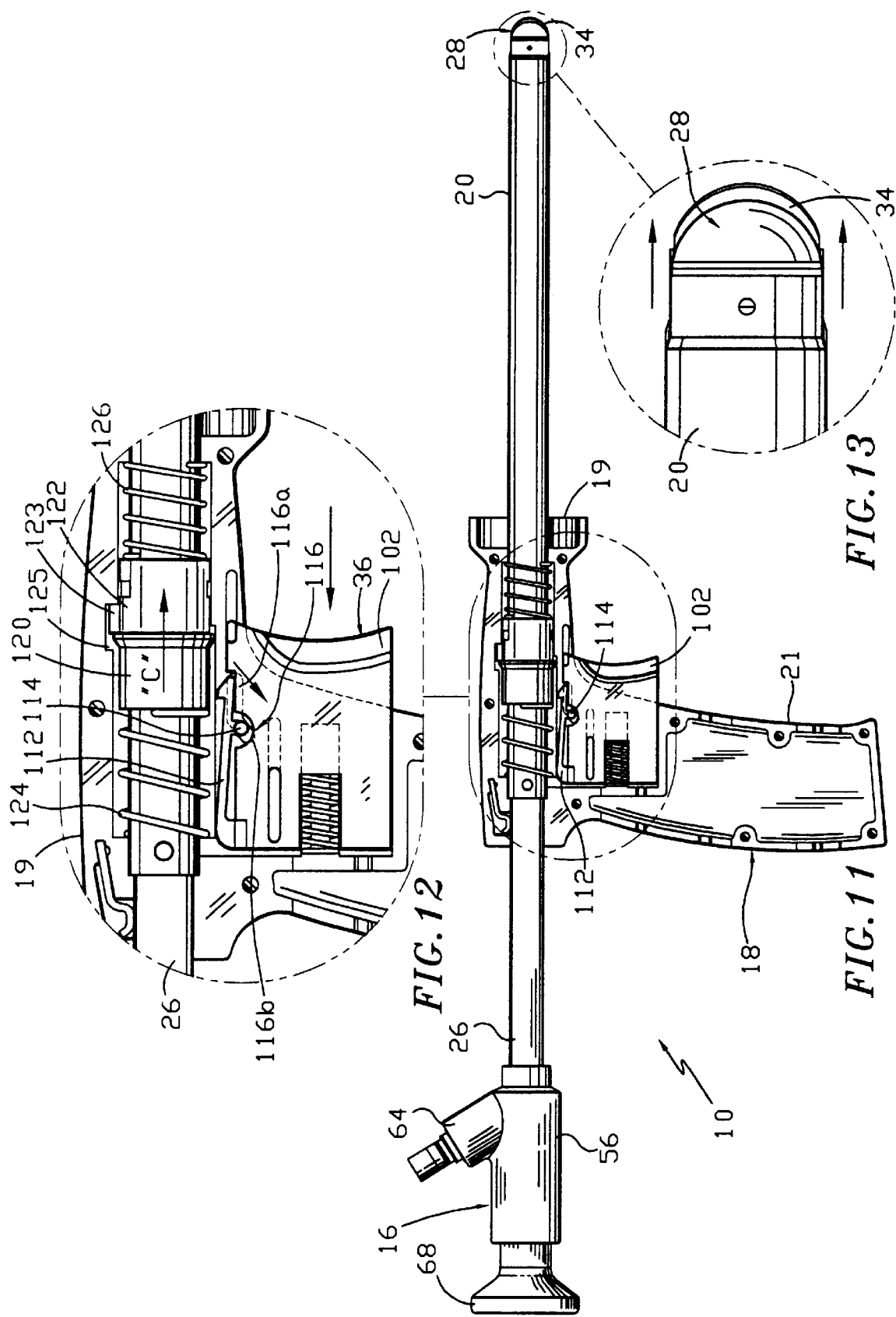

OPTICAL TROCAR

This is a continuation of U.S. application Ser. No. 08/249,707, filed on May 26, 1994, now abandoned.

BACKGROUND

1. Technical Field

An apparatus for penetrating and for observing penetration of body tissue is provided. More particularly, an optical trocar assembly is provided having a reciprocating cutting blade responsive to actuation of a trigger mechanism, which facilitates penetration of the peritoneum or other body tissue under direct observation.

2. Description of Related Art

Endoscopic surgical procedures, that is, surgical procedures performed through tubular sleeves or cannulas, have been utilized for many years. Initially, endoscopic surgical procedures were primarily diagnostic in nature. More recently as endoscopic technology has advanced, surgeons are performing increasingly complex and innovative endoscopic surgical procedures. In endoscopic procedures, surgery is performed in any hollow viscus of the body through a small incision or through narrow endoscopic tubes (cannulas) inserted through small entrance wounds in the skin. In laparoscopic procedures surgery is performed in the interior of the abdomen.

Laparoscopic procedures generally utilize instrumentation that is internally sealed to inhibit gases from entering or exiting the body through the laparoscopic or endoscopic incision. This is particularly true in surgical procedures in which the surgical region is insufflated. Moreover, laparoscopic and endoscopic procedures often require the surgeon to act on organs, tissues and vessels far removed from the incision, thereby requiring that any instruments to be used in such procedures be of sufficient size and length to permit remote operation. Typically, after the surgical region is insufflated, trocars are used to puncture the body cavity and include a cannula which remains in place for use during endoscopic procedures. Generally, trocars used during such procedures include a stylet having a sharp tip for penetrating the body cavity positioned coaxially within protective tubes to protect a patient or surgeon from inadvertent contact with the tip. An example of a known trocar is described in commonly assigned, U.S. Pat. No. 4,601,710 to Moll. Most currently used trocars rely on protective tubes or relative retraction of the tip to prevent inadvertent contact with tissue.

It would be advantageous to provide a trocar assembly for observing the penetration of the peritoneum or other body portions. The trocar assembly described herein provides an improved objective optical member for passing optical images to an imaging system, and an improved trigger mechanism for selectively reciprocating a cutting tip which facilitates penetration of body tissue. The objective optical member in combination with the imaging system provide a clear and bright image of the body tissue being penetrated as well as the cavity entered.

SUMMARY

A blade actuating assembly is provided which permits selective deployment of a tissue cutting blade positioned at a distal end of an optical trocar assembly configured to penetrate body tissue under direct observation. The blade actuating assembly includes at least one blade pusher member associated with an obturator sleeve, a blade drive mechanism connected to the blade pusher member and configured to alternately move the blade between deployed and non-deployed positions. A blade drive latch is provided to facilitate movement of the blade drive mechanism to an armed position and to releasably maintain the blade drive mechanism in the armed position. The blade actuating assembly also includes a trigger which is operatively connected to the blade drive latch and movable relative to the blade drive mechanism. In this configuration, movement of the trigger a first predetermined distance causes the blade drive latch to move the blade drive mechanism to the armed position, and movement of the trigger a second predetermined distance releases said blade drive latch from the blade drive mechanism to allow the blade drive mechanism to retract and withdraw the tissue cutting blade to a covered position within the distal end of the optical trocar assembly.

The trocar described herein includes a cannula assembly, an obturator assembly and an image passing system. The cannula assembly includes a cannula housing and a cannula sleeve extending from said cannula housing. The obturator assembly includes an obturator sleeve having a proximal end, a distal end and a longitudinal bore therebetween which are configured for coaxial alignment with the cannula assembly.

An image passing member or objective optical member is positioned at the distal end of the obturator sleeve and is provided to permit passage of optical images into the longitudinal bore of the sleeve and permit passage of illumination light to body tissue.

In a preferred embodiment, the objective optical member is a substantially hemispherical shaped or dome-shaped optical window which receives the optical images. Alternatively, the objective optical member is a dome-shaped lens which receives and directs the optical images into the obturator sleeve. The hemispherical or dome-shaped optical window advantageously is a traumatic to tissue.

An image transferring member, such as an endoscope, is preferably removably positioned within the longitudinal bore of the obturator sleeve and is provided to transmit illumination light through the image passing member to the surgical site and to transmit optical images from the image passing member to a proximal end of the obturator housing for subsequent viewing by the surgeon.

An actuating mechanism is provided to move a cutting blade at the distal end of the obturator sleeve. The actuating mechanism includes a blade advancing mechanism which is operatively connected to the blade and configured to move the blade between non-deployed and deployed positions. The actuating mechanism also includes a trigger mechanism which is operatively connected to the blade advancing mechanism and which includes at least one trigger movable between non-actuating and actuating positions. In this configuration, movement of the trigger to the actuating position, causes the blade advancing mechanism to move the blade to the deployed position. The blade advancing mechanism includes a hammer, a bushing and a drive spring, which are configured so that movement of the trigger to the actuating position permits the drive spring to move the hammer and bushing in a distal direction so as to move the blade to the deployed position.

BRIEF DESCRIPTION OF THE DRAWINGS

Preferred embodiments are described hereinbelow with reference to the drawings wherein:

FIG. 4 is a side view in partial cross-section of the obturator assembly and endoscope of FIG. 1, illustrating the trigger assembly;

FIG. 5 is an enlarged side view of the trigger assembly of the apparatus of FIG. 4, illustrating the trigger in a non-actuated position;

FIG. 6 is an enlarged assembled view of the distal end of the obturator assembly of FIG. 2, illustrating the interconnection between blade pusher arms and the blade;

FIG. 7 is a sectional assembled view of a portion of the trigger assembly of FIG. 2, illustrating the interconnection of the blade pusher arms to the trigger assembly;

FIG. 8 is a side view in partial cross-section of the obturator assembly and endoscope of FIG. 1, illustrating partial actuation of the trigger assembly with the blade in the non-deployed position;

FIG. 9 is an enlarged side view of the trigger assembly of FIG. 8;

FIG. 10 is an enlarged view of the distal end of the obturator assembly of FIG. 8, illustrating a dome-shaped objective optical member with the blade in the non-deployed position;

FIG. 11 is a side view in partial cross-section of the obturator assembly and endoscope of FIG. 1, illustrating actuation of the trigger assembly and the blade in the deployed position;

FIG. 12 is an enlarged side view of the trigger assembly of FIG. 11; and

FIG. 13 is an enlarged view of the distal end of the obturator assembly of FIG. 11, illustrating the dome-shaped objective optical member and the blade in the deployed position.

DETAILED DESCRIPTION OF THE PREFERRED EMBODIMENTS

An apparatus is provided to penetrate body tissue, e.g., the abdominal wall, and to provide a simultaneous forward directional view of the body tissue being penetrated. In a preferred embodiment, shown in FIG. 1, the apparatus includes a trocar assembly 10 having an obturator assembly 12, a cannula assembly 14, and an image transmitting member, such as endoscope 16. Endoscope 16 is positioned within the obturator assembly 12 to provide observation of the body tissue being penetrated. The term obturator assembly as used herein refers to the tissue penetrating assembly of the trocar assembly 10.

Figure 1:
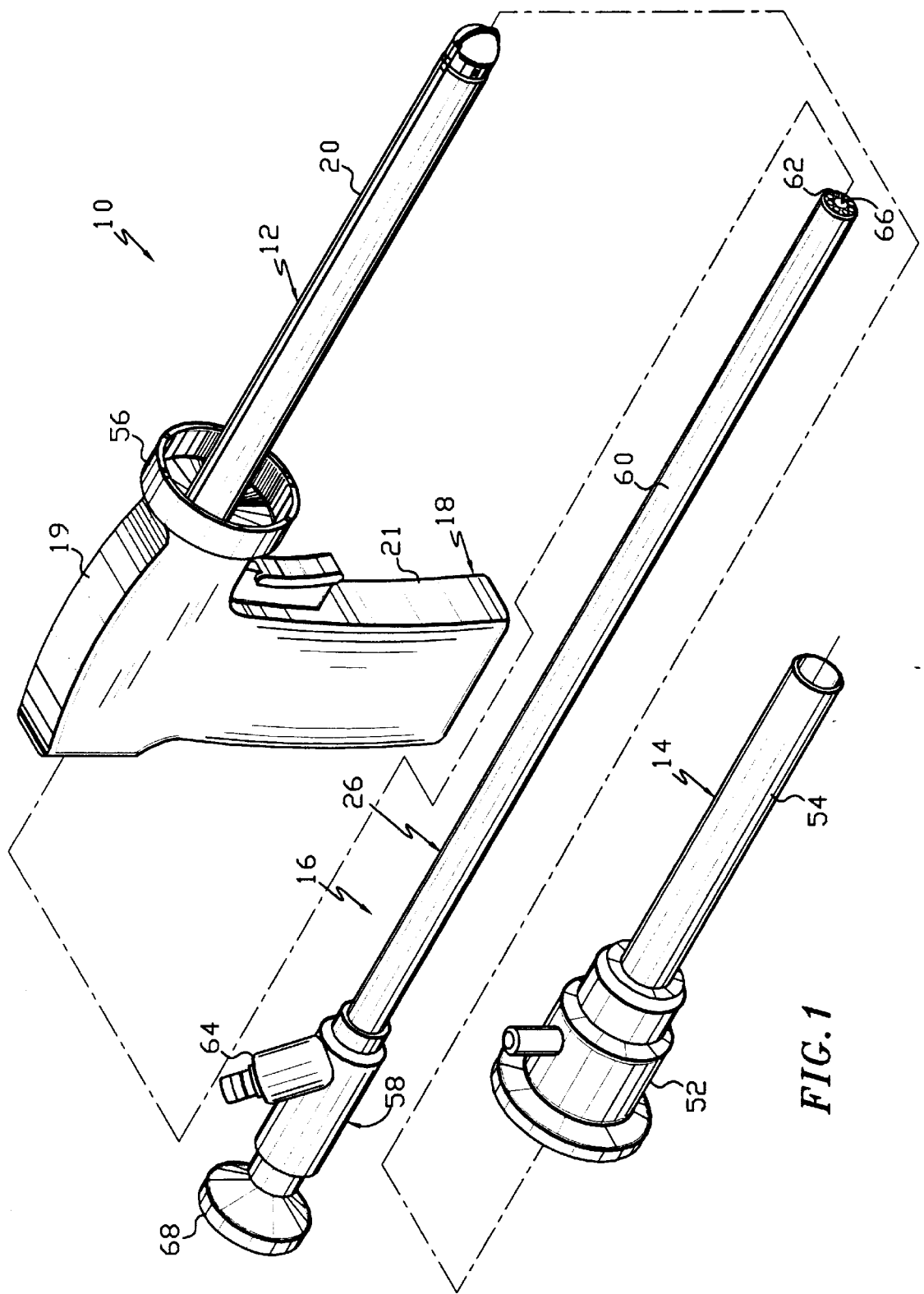
FIG. 1 is a perspective view with parts separated of the optical trocar, illustrating a cannula assembly, an obturator assembly, and an endoscope.
Figure 2:
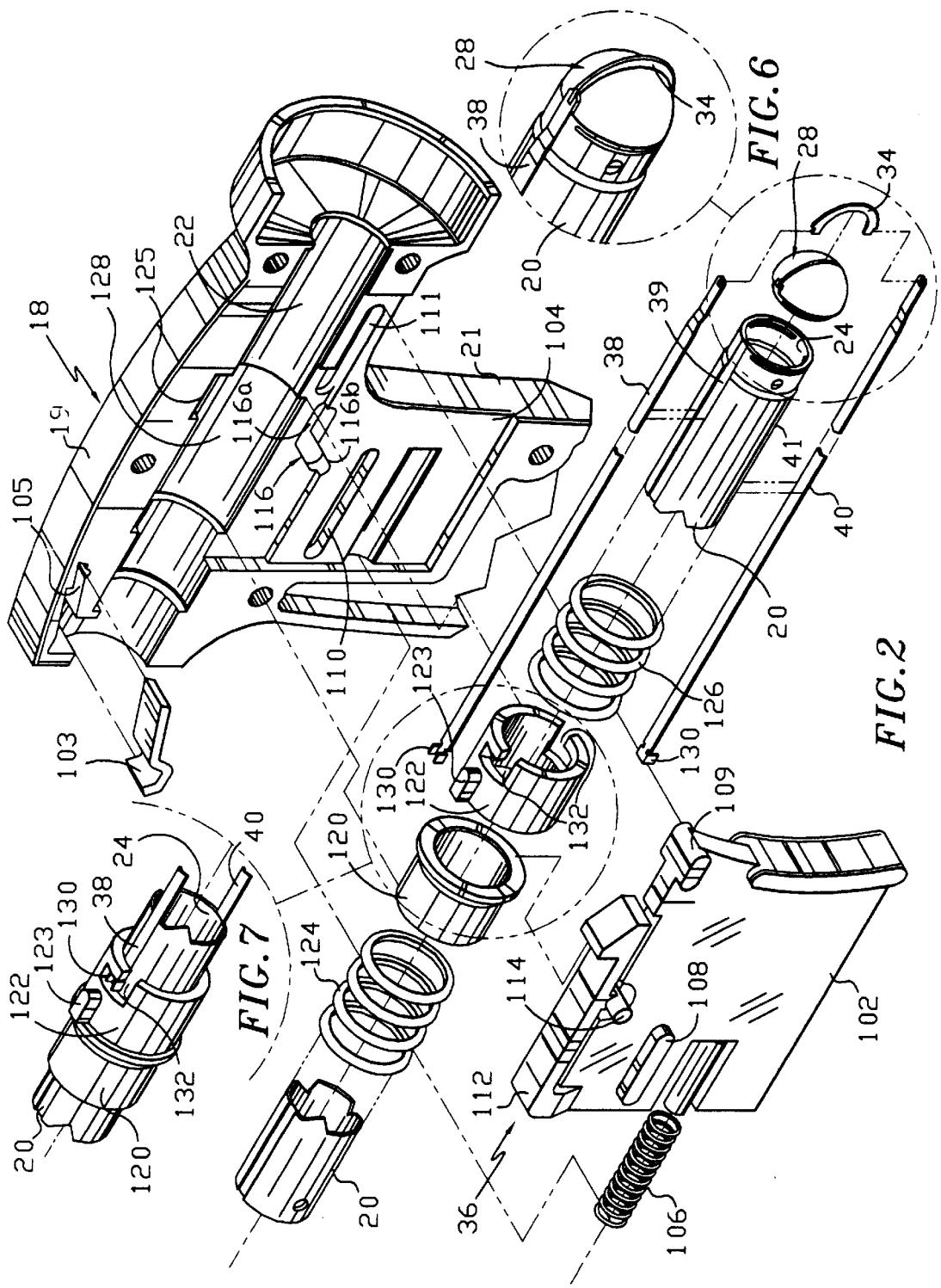
FIG. 2 is an exploded view of a portion of the obturator assembly of FIG. 1, illustrating a trigger assembly for deploying a blade.

Referring to FIGS. 1 and 2, obturator assembly 12 includes housing 18 and a longitudinally extending obturator sleeve 20. Obturator housing 18 includes barrel portion 19 and hand grip 21. The proximal end of obturator sleeve 20 is secured within channel 22 of barrel portion 19 so that the obturator sleeve 20 extends outwardly from the obturator housing 18. Hand grip 21 is provided for manual gripping to facilitate penetration of the body tissue.

Obturator sleeve 20 has a longitudinal bore 24 which extends between the proximal end and distal end. The longitudinal bore 24 is configured and dimensioned to receive the endoscopic portion 26 of the endoscope 16, as shown in FIG. 1. Housing 18 of obturator assembly 12 is constructed of two half-sections which are joined together by welding, adhesives or the like. Leaf spring 103 is positioned within channel 105 at the proximal end of the barrel portion 19 of housing 18, as shown in FIG. 2. Leaf spring 103 is provided to engage endoscopic portion 26 of endoscope 16, to frictionally maintain the endoscope in a fixed longitudinal relationship with respect to obturator sleeve 20.

Figure 3:
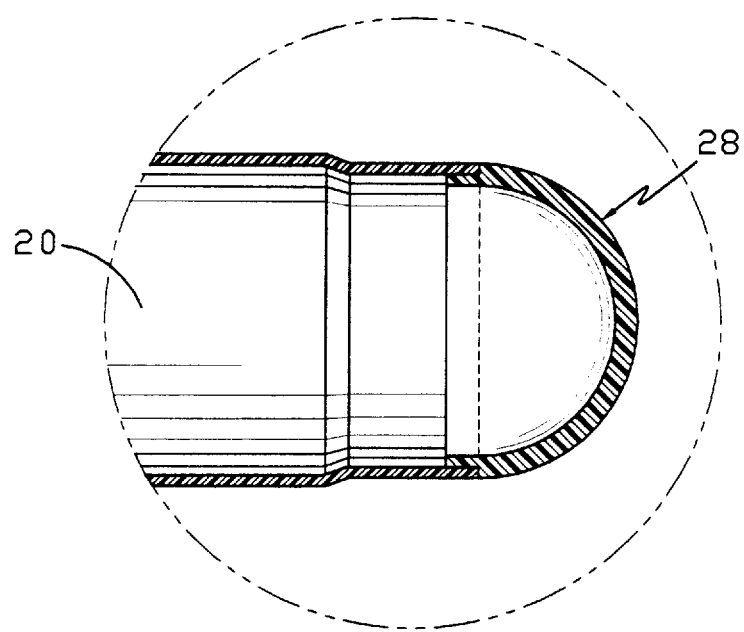
FIG. 3 is a cross-sectional view of the distal end of the obturator assembly of FIG. 1, illustrating an objective optical member positioned at the distal end thereof.

Referring to FIGS. 2 and 3, an image passing member 28 is secured to the distal end of obturator sleeve 20 and is provided to permit or direct images into the obturator sleeve 20 and to allow for the passage of illumination light from the obturator sleeve 20 to body tissue. The image passing member 28 may be a transparent optical window or an optical lens fabricated from a variety of materials such as polystyrene, polymethylmethacrylate (PMMA), polyurethane, transparent epoxies and/or glass or other transparent materials. The optical window shown in this preferred embodiment is hemispherical shaped, i.e., dome-shaped, and capable of allowing optical images to pass therethrough and into the longitudinal bore 24 of obturator sleeve 20, so as to impinge the distal end of endoscope 16.

The objective optical member is also a dome-shaped member. However in this configuration, optical images which impinge the dome-shaped surface of objective optical member 28 are directed into longitudinal bore 24 of obturator sleeve 20, so as to impinge the distal end of endoscope 16. The objective optical member as well as the optical window are preferably configured to allow approximately a full forward angle of view.

Referring again to FIG. 2, the cutting portion 32 of obturator assembly 12 includes a cutting blade 34 connected to actuating assembly 36. The cutting blade 34 shown in this preferred embodiment is arcuate in shape so as to conform to the outer surface of the dome-shaped image passing member 28. Blade 34 interfits within an arcuate recess in the dome-shaped image passing member 28 when in the non-deployed position. The cutting blade 34 is preferably centered with respect to the outer surface of the image passing member as shown. Thus, in visualization, the cutting blade is seen as a thin line through the center, i.e. bisecting, the viewing field so as not to obstruct viewing of the body.

Referring now to FIGS. 2, 4, 5 and 6, actuating assembly 36 is contained within housing 18 and is provided to move blade 34 between a non-deployed position (FIG. 4) and a deployed position (FIG. 6) which will be described in more detail below. As shown in FIG. 2, the actuating assembly 36 includes a trigger 102 slidably positioned within channel 104 in housing 18 and movable between non-actuating and actuating positions. Spring 106 is secured between housing 18 and trigger 102 so as to normally bias the trigger to the non-actuating position, shown in FIG. 5. Alignment fingers 108 and 109 extend from trigger 102 into corresponding channels 110 and 111 within housing 18. Alignment fingers 108 and 109 are provided to maintain the alignment of trigger 102 within channel 104 of housing 18.

Hammer blade drive latch 112 is secured to or extends integrally therefrom trigger 102 and includes a latch release member, in the form of post 114. Post 114 extends between the two housing halves and into corresponding channels 116 of each housing half, as shown in FIG. 5. Channels 116 include a longitudinal portion 116a which permits the hammer latch 112 to engage the hammer, and a sloped portion 116b which causes hammer latch 112 to disengage from the hammer, as will be described in more detail below.

Referring again to FIGS. 2 and 5, the actuating assembly 36 also includes blade drive members, such as hammer 120, bushing 122 and a pair of drive springs 124 and 126. As shown in FIG. 5, the hammer, bushing and drive springs are coaxially aligned with obturator sleeve 20. Drive spring 124 is positioned about obturator sleeve 20 within channel 128 of each housing half so that one end of the spring engages the housing and the other end engages the proximal end of hammer 120. Drive spring 124 normally biases hammer 120 toward the distal end of the obturator assembly 12, indicated by arrow "A" in FIG. 5. The proximal end of bushing 122 is positioned adjacent hammer 120 and the distal end of bushing 122 engages one end of drive spring 126. The other end of drive spring 126 engages the housing 18, as shown. Finger 123 extending from bushing 122 into channel 125 within housing 18, are provided to limit the proximal and distal movement of the bushing 122 and thus the proximal and distal movement of blade 34.

Referring to FIGS. 2 and 7, blade pusher arms 38 and 40 are positioned in slots 39 and 41, respectively, within the obturator sleeve 20. The proximal end of each blade pusher arm includes fingers 130 extending outwardly therefrom which are configured to slide within corresponding notches 132 in bushing 122 to releasably secure the blade pusher arms 38 and 40 to bushing 122, as shown in FIG. 7.

Referring to FIGS. 8–13, in the above configuration, movement of trigger 102 in the proximal direction, shown by arrow "B" in FIGS. 8 and 9, causes hammer latch 112 to retract hammer 120 and compress drive spring 124 (i.e., the hammer latch moves the hammer to a cocked or armed position). Post 114 is within the longitudinal portion 116a of channel 116 and blade 34 continues to remain in the non-deployed (i.e., retracted) position within objective optical member 28, as shown in FIG. 10. Further proximal movement of trigger 102 causes post 114 to move in a downward direction within the sloped portion 116b of channel 116, as shown in FIGS. 11 and 12. Downward movement of post 114 causes hammer latch 112 to disengage from hammer 120 so that hammer 120 is thrusted distally (i.e., in the direction of arrow "C") by drive spring 124. As hammer 120 moves distally, the hammer engages bushing 122 and thrusts the bushing distally so as to move blade 34 to the deployed (i.e., exposed) position, as shown in FIGS. 11 and 13. Distal movement of bushing 122 also compress drive spring 126 and when the biasing force of drive spring 126 exceeds the compression force exerted by the hammer 120, drive spring 126 automatically biases bushing 124 proximally so that blade 34 is automatically returned to the non-deployed position. Thus, engagement of hammer 120 and bushing 122 provides substantially instantaneous deployment and retraction of the blade so the blade remains exposed for a short period of time. Thus, once the trigger is pulled to a predetermined position, the blade is deployed and then retracted without further action of the user (i.e., without further movement of the trigger).

In the configuration described, the actuation assembly 36 operates in a two step manner. In the first step, trigger 102 is moved proximally to cock hammer 120. In the second step, further proximal movement of trigger 102 causes the hammer 120 to automatically move distally to advance the blade 34 to the deployed position, and the blade is automatically returned to the non-deployed position under the force of drive spring 126. This two step manner automatically occurs upon fully squeezing the trigger 102.

Referring again to FIG. 1, cannula assembly 14 includes cannula housing 52 and cannula sleeve 54 secured to the cannula housing 52 and extending outwardly therefrom. Barrel portion 19 of obturator housing 18 includes bushing 56 which is configured and dimensioned to interfit with the proximal end of cannula housing 52, so that obturator sleeve 20 coaxially aligns with cannula sleeve 54 when the two assemblies are interfitted. The cannula sleeve 54 is adapted to remain in the body after penetration and subsequent removal of the obturator assembly 12 (and endoscope 16) to allow insertion of appropriate endoscopic/laparoscopic instrumentation therethrough.

To maintain a gas tight seal within the cannula housing, a sealing member or system may be positioned therewithin which is adapted to receive the obturator assembly 12 of the present invention as well as other endoscopic surgical instruments. One example of a suitable sealing system utilizes a duckbill sealing member. A more detailed description of an exemplary cannula assembly and sealing system is found in U.S. Pat. No. 5,180,373 issued Jan. 19, 1993, which is incorporated herein by reference.

Continuing to refer to FIG. 1, endoscope 16 includes endoscopic portion 26 and endoscope housing 58. Endoscopic portion 26 is configured to transfer illuminating light from endoscope housing 58 to the distal end of the endoscopic portion to provide illuminating light to the operative site. In an exemplary configuration, endoscopic portion 26 includes an outer sheath 60 and an annular array of fiber optic elements 62 extending between light source connector 64 of endoscope housing 58 and the distal end of outer sheath 60 to illuminate the operative site. Any known light source may be connected to connector 64 to provide the illuminating light.

Endoscopic portion 26 includes an image transferring system 66 which may include CCD's, a bundle of fiber optic elements or objective lenses which transfer an optical image received at the distal end of endoscope 16 to eyepiece 68 for viewing. Alternatively, a video system including a monitor may be operatively connected to housing 58 to provide a video image of the body tissue being penetrated.

Preferably, the fiber optic elements 62 are positioned adjacent the inner wall of the outer sheath so as to surround the image transferring system. In this configuration, illumination light from the endoscope is passed through the image passing member 28 and optical images which impinge the image passing member 28 pass into the image transferring system and are relayed to eyepiece 68. An example of an endoscope which can be utilized is described in U.S. Pat. No. 4,964,710 incorporated herein be reference.

In an alternate embodiment, the obturator assembly 12 and endoscope 16 or optical components thereof can be a single unit inserted into cannula assembly 14. For example, the obturator assembly can be manufactured with illumination optics and/or imaging optics positioned therein so that the obturator assembly itself can function to penetrate tissue as well as to light the surgical site and transmit images to the video monitor. In this version, the obturator would not have a longitudinal bore and it would be sealed.

In operation, endoscope 16 is inserted into the trocar assembly 10, i.e. into longitudinal bore 24 of obturator sleeve 20, as shown in FIG. 4. The surgeon then positions the blade 34 against the body tissue and repeatedly moves blade 34 by continuously squeezing trigger 102 to automatically move the blade 34 rapidly from the nondeployed position to the deployed position and back to the non-deployed position. Pressure is applied to hand grip 21 in the distal direction to penetrate the body tissue. The movement of blade 34 facilitates controlled cutting of the body tissue, thus permitting the surgeon to apply relatively minimal pressure to hand grip 21 to penetrate the body tissue. During penetration of the body tissue the surgeon either observes such penetration through eyepiece 68, or in instances where a video system is utilized the surgeon simply observes the penetration of the body tissue via any known video monitor.

Alternatively, the surgeon may also more selectively deploy the blade 34 during penetration. That is, the surgeon may insert the trocar assembly and bluntly penetrate the body tissue until reaching thicker tissue, such as muscle. At this point, the blade can be deployed to penetrate (cut through) this thick tissue. When thick tissue is again encountered, the blade can be deployed again. After penetration into the body cavity, both the endoscope 16 and the obturator assembly 12 are removed from the cannula assembly 14, leaving the cannula assembly 14 in the body for insertion of desired instrumentation therethrough.

It will be understood that various modifications can be made to the embodiments herein disclosed without departing from the spirit and scope thereof. For example, various diameters for the cannula assembly, the obturator assembly, as well as various diameter endoscopes are contemplated. Also, various modifications may be made in the configuration of the trigger assembly to achieve the instantaneous deployment and retraction of the blade. Therefore, the above description should not be construed as limiting but merely as exemplifications of preferred embodiments thereof. Those skilled in the art will envision other modifications within the scope and spirit of the claims appended hereto.

What is claimed is:

1. A blade actuating assembly for selectively deploying a blade from a distal end of a trocar having a cannula assembly, an obturator assembly having an obturator housing and obturator sleeve connected to the housing and having a longitudinal axis, and an objective optical member positioned at a distal end of the obturator assembly, said blade actuating assembly comprising:

at least one blade pusher member having proximal and distal end portions, said distal end portion being longitudinally movable to move the blade between deployed and nondeployed positions;

a blade drive mechanism operatively connected to said proximal end portion of said at least one blade pusher member and configured to alternately move the blade between the deployed and non-deployed positions;

a blade drive latch configured to facilitate movement of said blade drive mechanism to an armed position and to releasably maintain said blade drive mechanism in said armed position; and a trigger operatively connected to said blade drive latch and movable relative to said blade drive mechanism such that movement of said trigger a first predetermined distance causes said blade drive latch to move said blade drive mechanism to said armed position, and movement of said trigger a second predetermined distance releases said blade drive latch from said blade drive mechanism to actuate said blade drive mechanism.

2. The blade actuating assembly according to claim 1, wherein said blade drive mechanism comprises:

a bushing connected to said at least one blade pusher member; and means for moving said bushing in alternating directions such that the blade is moved to said deployed position and to said non-deployed position.

3. The blade actuating assembly according to claim 1, wherein said blade drive latch and said trigger are integral.

4. A trocar which comprises:

a cannula;

an obturator configured for insertion into said cannula, said obturator having a proximal end, a distal end and a longitudinal bore;

an objective optical member positioned at said distal end of said obturator for collecting optical images for conveyance into said longitudinal bore; and an actuating mechanism for moving a blade positioned at said distal end of said obturator, said actuating mechanism including:

a blade advancing mechanism operatively connected to said blade and configured to selectively reciprocate said blade relative to the obturator between a deployed position and a non-deployed position; and a trigger mechanism operatively connected to said blade advancing mechanism and including at least one trigger movable between non-actuated and actuated positions, such that following movement of said trigger to said actuated position, said blade advancing mechanism to advance and retracts causing said blade to reciprocate.

5. The trocar according to claim 4, wherein said objective optical member is an optical lens having a substantially hemispherical outer surface for receiving and directing optical images.

6. The trocar according to claim 5, wherein said blade is arcuate in shape so as to conform to said substantially hemispherical outer surface of said optical lens.

7. The trocar according to claim 4, wherein said objective optical member is an optical window having a substantially hemispherical outer surface for receiving optical images.

8. The trocar according to claim 7, wherein said blade is arcuate in shape so as to conform to said substantially hemispherical outer surface of said optical window.

9. The trocar according to claim 4, wherein said actuating mechanism provides two step operation for deploying said blade, wherein in a first step, actuation of said trigger causes said blade advancing mechanism to move to an armed position, and in a second step said blade advancing mechanism is released from said armed position upon movement of said trigger to said actuator position.

10. An obturator for facilitating insertion into body tissue under direct observation, which comprises:

a sleeve having a proximal end, a distal end and a longitudinal bore.

a dome-shaped objective optical member positioned at said distal end of said sleeve for collecting optical image for conveyance into said longitudinal bore;

a blade mounted in a recess in said objective optical member and movable relative to the optical member;

blade advancement structure position in the sleeve;

blade retraction structure positioned in the sleeve; and an actuator operatively connected to the blade, such that following movement of the actuator to an actuation position, the blade moves from a non-deployed position to a deployed position and automatically returns to the non-deployed position.

11. The obturator according to claim 10, wherein said objective optical member is an optical window.

12. The obturator according to claim 10, wherein said objective optical member is an optical lens.

13. The obturator according to claim 10 further comprising an image transferring member positioned at least partially within said longitudinal bore of said sleeve and adjacent said objective optical member for transmitting images conveyed into said longitudinal bore to said proximal end of said sleeve.

14. The obturator according to claim 13, wherein said image transferring member comprises an endoscope removably positioned within said longitudinal bore.

15. Apparatus for penetrating body tissue comprising:
   a cannula having a longitudinal bore;
   an obturator removably positioned in said bore of said cannula, said obturator having an objective optical member positioned thereon;
   a cutting blade movably positioned at a distal end of said obturator; and
   an actuating mechanism operatively connected to said cutting blade;
   wherein said actuating mechanism is movable between first and second positions, such that following movement of said actuating mechanism from said first position to said second position, said blade automatically moves relative to the obturator from a retracted position to an extended position and back to said retracted position such that the blade cannot be maintained by the user in the extended position.

16. The apparatus according to claim 15, wherein said actuating mechanism includes a trigger operatively connected to a blade advancing mechanism which are configured to selectively reciprocate said blade between said retracted position and said extended position.

17. The apparatus according to claim 15 further comprising an image transmitting member positioned within said obturator and adjacent said objective optical member for transmitting images passed through said objective optical member to a proximal end of said obturator for viewing.

18. The apparatus according to claim 17, wherein said image transmitting member comprises an endoscope removably positioned within a longitudinal bore in said obturator.

19. The apparatus according to claim 15, wherein said objective optical member includes a dome-shaped outer surface.

20. The apparatus according to claim 19, wherein said cutting blade is arcuate in shape to conform to said dome-shaped outer surface of said objective optical member.

21. A trocar which comprises:
   a cannula;
   an obturator configured for insertion into said cannula, said obturator having a proximal end, a distal end and a longitudinal bore;
   an objective optical member positioned at said distal end of said obturator for collecting optical images for conveyance into said longitudinal bore; and
   an actuating mechanism for moving a blade positioned at said distal end of said obturator, said actuating mechanism including:
   a blade advancing mechanism operatively connected to said blade and configured to selectively reciprocate said blade relative to the obturator between a deployed position and a nondeployed position; and a trigger mechanism operatively connected to said blade advancing mechanism and including at least one trigger movable between non-actuated and actuated positions, such that movement of said trigger to said actuated position releases the blade advancing mechanism to cause said blade advancing mechanism to advance and then to retract the blade to its non-deployed position.

22. An obturator for facilitating insertion into body tissue under direct observation, which comprises:
   a sleeve having a proximal end, a distal end and a longitudinal bore;
   a dome-shaped objective optical member positioned at said distal end of said sleeve for collecting optical images for conveyance into said longitudinal bore;
   a blade mounted in a recess in said objective optical member and movable relative to the optical member;
   blade advancement structure positioned in the sleeve;
   blade retraction structure positioned in the sleeve; and
   an actuator operatively connected to the blade, wherein movement of the actuator to an actuation position initially retracts a portion of the blade advancement structure, then advances the blade advancement structure moving the blade from a non-deployed position to a deployed position and back to the non-deployed position.

23. Apparatus for penetrating body tissue comprising:
   a cannula having a longitudinal bore;
   an obturator removably positioned in said bore of said cannula, said obturator having an objective optical member positioned thereon;
   a cutting blade movably positioned at a distal end of said obturator; and
   an actuating mechanism operatively connected to said cutting blade;
   wherein said actuating mechanism is movable in a range of movement between first and second positions, such that movement of said actuating mechanism from said first position to said second position automatically moves said blade relative to the obturator from a retracted position to an extended position and back to said retracted position, the actuating mechanism being configured such that during the entire range of movement of the actuating mechanism the blade is prevented from being maintained in the extended position.

* * * * *